United States Patent
Alleyne et al.

(10) Patent No.: US 7,294,128 B2
(45) Date of Patent: Nov. 13, 2007

(54) BONE FIXATION APPARATUS

(75) Inventors: Neville Alleyne, La Jolla, CA (US); Makoto Nonaka, La Jolla, CA (US)

(73) Assignee: NAS Medical Technologies, Inc., San Diego, CA (US)

( * ) Notice: Subject to any disclaimer, the term of this patent is extended or adjusted under 35 U.S.C. 154(b) by 232 days.

(21) Appl. No.: 10/411,075

(22) Filed: Apr. 8, 2003

(65) Prior Publication Data

US 2004/0030337 A1    Feb. 12, 2004

Related U.S. Application Data

(60) Provisional application No. 60/371,602, filed on Apr. 9, 2002.

(51) Int. Cl.
*A61B 17/56* (2006.01)
*A61F 2/30* (2006.01)

(52) U.S. Cl. ...................................................... 606/61

(58) Field of Classification Search ................ 606/60, 606/61, 72, 73; 215/330; 220/290, 296
See application file for complete search history.

(56) References Cited

U.S. PATENT DOCUMENTS

| | | | |
|---|---|---|---|
| 4,805,602 A | 2/1989 | Puno et al. | |
| 5,346,493 A * | 9/1994 | Stahurski et al. | 606/61 |
| 5,360,431 A | 11/1994 | Puno et al. | |
| 5,443,467 A * | 8/1995 | Biedermann et al. | 606/65 |
| 5,466,237 A | 11/1995 | Byrd et al. | |
| 5,474,555 A | 12/1995 | Puno et al. | |
| 5,496,321 A | 3/1996 | Puno et al. | |
| 5,609,594 A | 3/1997 | Errico et al. | |
| 5,624,442 A | 4/1997 | Mellinger et al. | |
| 5,669,911 A | 9/1997 | Errico et al. | |
| 5,681,319 A * | 10/1997 | Biedermann et al. | 606/104 |
| 5,725,528 A | 3/1998 | Errico et al. | |
| 5,735,851 A | 4/1998 | Errico et al. | |
| 5,752,957 A | 5/1998 | Ralph et al. | |
| 5,782,833 A | 7/1998 | Haider | |
| 5,797,911 A | 8/1998 | Sherman et al. | |
| 5,800,435 A | 9/1998 | Errico et al. | |

(Continued)

FOREIGN PATENT DOCUMENTS

FR    2 810 533    12/2001

(Continued)

*Primary Examiner*—Anuradha Ramana
(74) *Attorney, Agent, or Firm*—Knobbe Martens Olson & Bear LLP

(57) ABSTRACT

A bone fixation apparatus adapted for use in spinal stabilization. The apparatus includes a threaded bone screw having a spherical head that is received in a receiver cup. The receiver cup also includes a slot or groove through which a support rod passes. A saddle is positioned in the receiver cup below the support rod and above the head of the threaded bone screw. Alignment flanges are positioned partially around an opening on the receiver cup opposite the bone screw. A cap having internal grooves corresponding to the alignment flanges mates with the receiver cup. The cap may be positioned onto the receiver cup in a first orientation and secured to the receiver cup by rotating approximately one quarter turn. A compression member is screwed into internal threads on an opening of the cup to provide pressure on the support rod, thereby fixing the rod to the receiver cup.

9 Claims, 7 Drawing Sheets

U.S. PATENT DOCUMENTS

| | | |
|---|---|---|
| 5,879,350 A | 3/1999 | Sherman et al. |
| 5,882,350 A | 3/1999 | Ralph et al. |
| 5,885,286 A | 3/1999 | Sherman et al. |
| 5,891,145 A | 4/1999 | Morrison et al. |
| 5,961,518 A | 10/1999 | Errico et al. |
| 5,997,539 A | 12/1999 | Errico et al. |
| 6,053,917 A | 4/2000 | Sherman et al. |
| 6,063,089 A | 5/2000 | Errico et al. |
| 6,077,262 A * | 6/2000 | Schlapfer et al. ............ 606/61 |
| 6,179,841 B1 | 1/2001 | Jackson |
| 6,280,442 B1 | 8/2001 | Barker et al. |
| 6,302,888 B1 | 10/2001 | Mellinger et al. |
| 6,402,752 B2 * | 6/2002 | Schaffler-Wachter et al. . 606/61 |
| 6,440,137 B1 * | 8/2002 | Horvath et al. ............... 606/73 |
| 6,443,953 B1 | 9/2002 | Perra et al. |
| 6,565,567 B1 * | 5/2003 | Haider ........................ 606/61 |
| 6,755,829 B1 * | 6/2004 | Bono et al. ................... 606/61 |
| 6,786,903 B2 * | 9/2004 | Lin ............................. 606/23 |

FOREIGN PATENT DOCUMENTS

| | | |
|---|---|---|
| WO | WO 91/16020 | 10/1991 |

\* cited by examiner

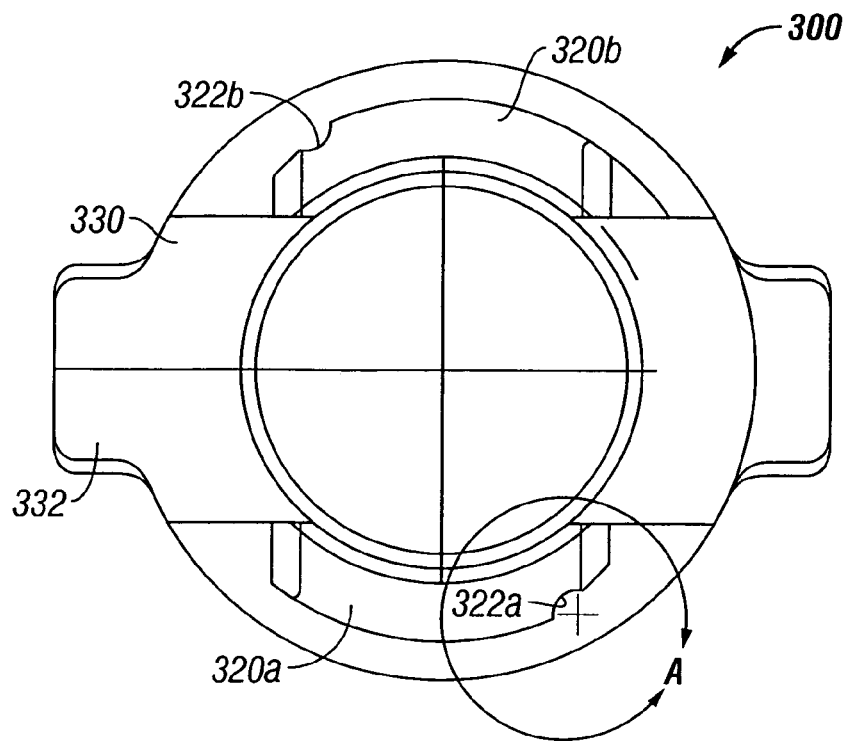
FIG. 4
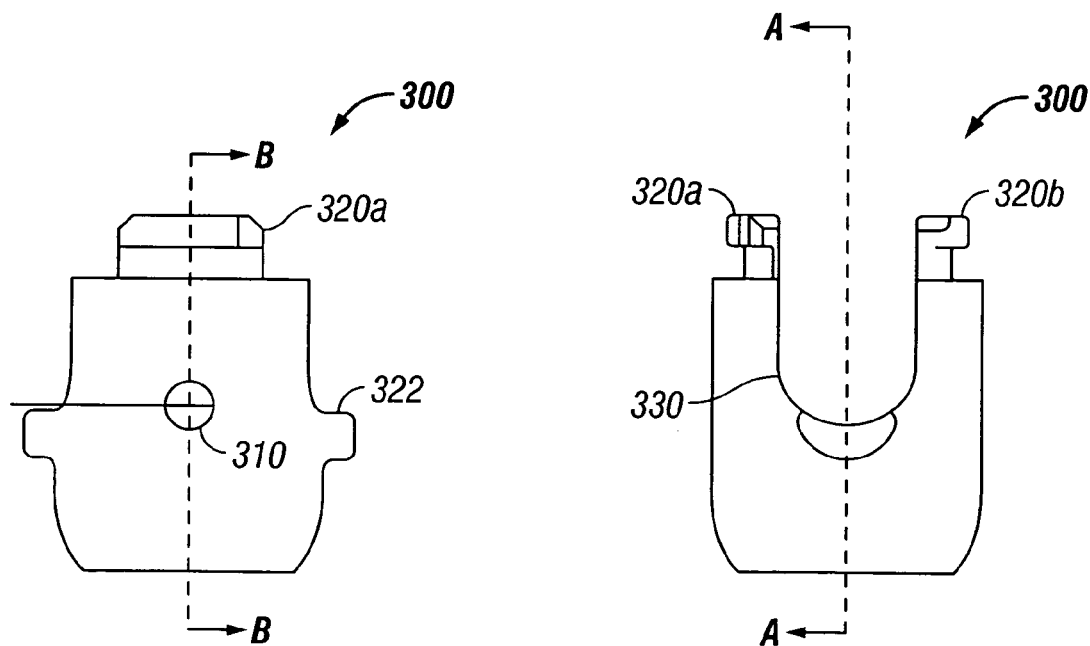
FIG. 5A  FIG. 5B

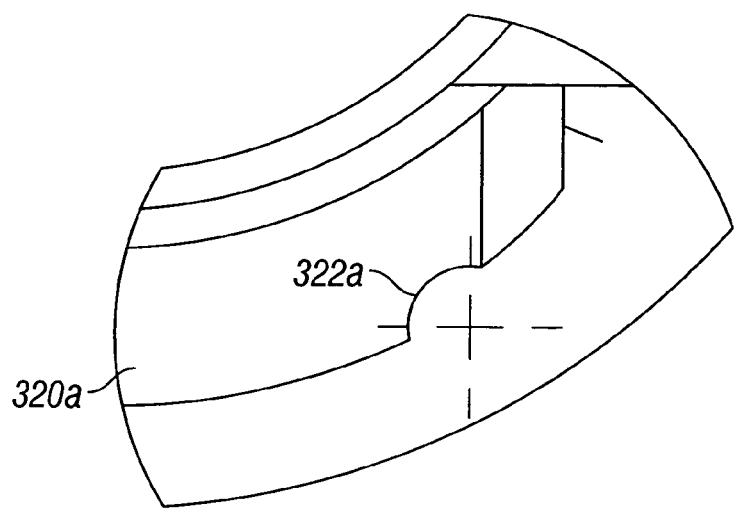
FIG. 6
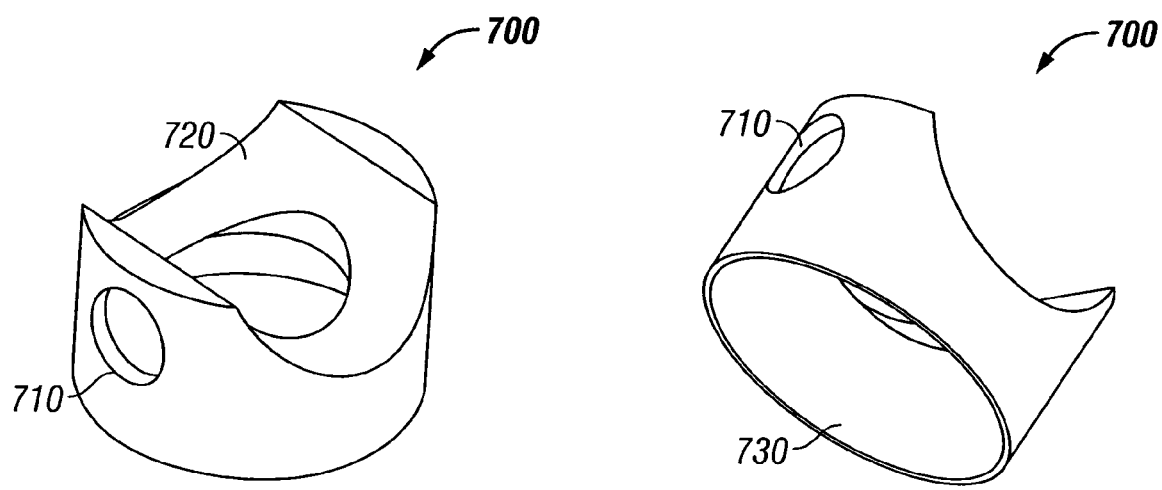
FIG. 7A          FIG. 7B

BONE FIXATION APPARATUS

RELATED APPLICATIONS

This application claims the benefit of U.S. Provisional Application No. 60/371,602, filed Apr. 9, 2002, entitled "SPINAL SCREW APPARATUS", the entirety of which is hereby incorporated herein by reference.

BACKGROUND OF THE INVENTION

1. Field of the Invention

The invention relates to the field of medical devices. More particularly, the invention relates to a bone fixation apparatus.

2. Description of the Related Art

Injuries to the spine can occur from fractures of vertebra, bulging or slipped disks, infections, tumors, and other sources. Patients with such injuries can experience considerable pain. Some types of spinal injuries may be corrected through spinal surgery. In one type of spinal surgery, two or more adjacent vertebrae are fused together.

In order to fuse two vertebrae together, an incision is made over the location to be fused. Bone and tissue are removed from the joint to allow the vertebrae to fuse together into one unitary segment. A bone graft may sometimes be inserted into the disk space. Metal rods may be used to stabilize the spine while the vertebrae fuse together.

The structures that are inserted into the vertebra are often threaded screws, and because of their position in the vertebra, are often referred to as pedicle screws. The pedicle screws are placed along two or more adjacent vertebra and are attached to a rod that is used to support and stabilize the spine.

Pedicle screws and the associated rod support structures are secured together with a coupler that includes a threaded fastener inserted into or onto the coupler during the course of the surgery. However, because the fastener is threaded into the support structure during the course of surgery, it can be difficult to mate the threads accurately in a tight surgical field and there is the possibility of cross threading the screw.

What is desired is a support structure for use with a bone fixation apparatus that allows a support rod to be fixed with the force of a threaded fastener, and that is easier to install.

SUMMARY

In one aspect, the invention comprises a bone fixation apparatus including a receiver cup including at least one receiver engagement portion and a cap including at least one cap engagement portion. The cap engagement portion slidably engages the at least one receiver engagement portion when the cap is rotated on the receiver cup less than one full rotation.

In another aspect of the invention, the bone fixation apparatus further includes a bone fastener having a head and a body with the head captured in the receiver cup and the body extending through the receiver cup, and a support rod having a portion extending into the receiver cup through at least one cutout in the receiver cup.

In still another aspect of the invention, the bone fixation apparatus further includes a compression member extending through the cap and configured to fix the position of the support rod relative to the receiver cup.

In another aspect of the invention, the bone fixation apparatus further includes a saddle interposed between the support rod and the head of the bone fastener.

In still another aspect, the invention comprises a method of stabilizing bones stabilizing bones including assembling a compression member to a cap away from a surgical field, capturing a head of a bone fastener in a receiver cup, inserting the bone fastener into a bone in the surgical field, and coupling the cap to the receiver cup in the surgical field by rotating the cap less than one full rotation relative to the receiver cup.

In still another aspect, the method further includes prior to coupling the cap to the receiver cup, capturing a portion of a support rod in the receiver cup and after coupling the cap to the receiver cup, compressing the portion of the support rod within the receiver cup using the compression member.

The compression member can compress the portion of the support rod by threading a threaded member into the cap.

BRIEF DESCRIPTION OF THE DRAWINGS

The above-described aspects and other aspects, features and advantages of the invention will be apparent upon review of the following detailed description and the accompanying drawings. In the drawings, like reference characters identify identical or functionally equivalent elements.

FIG. 4 is a top view of the receiver cup.

FIGS. 5A-5B are side views of the receiver cup.

FIG. 6 is a detail view of the flange of the receiver cup.

FIGS. 7A-7B are views of a saddle.

DETAILED DESCRIPTION OF EMBODIMENTS OF THE INVENTION

Embodiments of the invention will now be described with reference to the accompanying Figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

Figure 1:
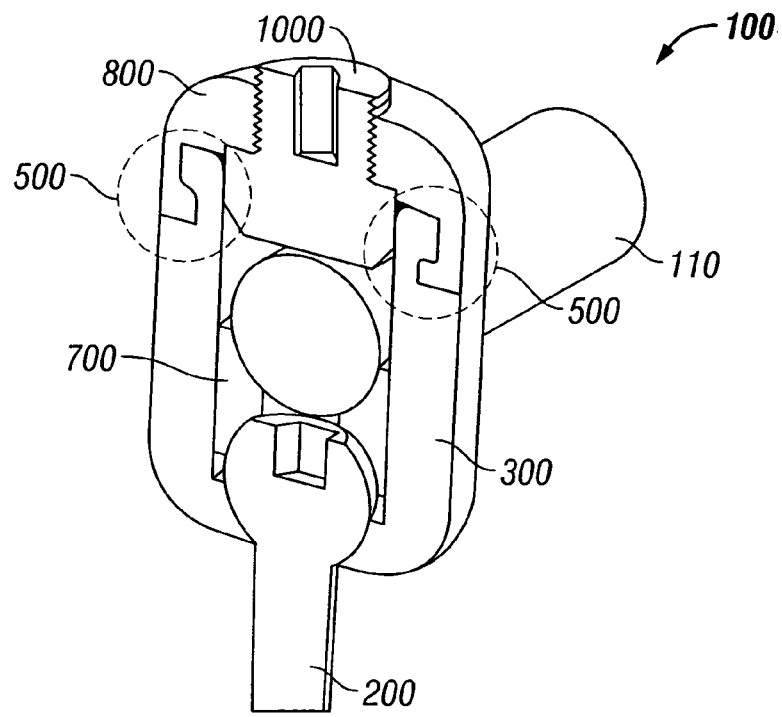
FIG. 1 is a section view of an embodiment of an assembled bone fixation apparatus.

FIG. 1 is a sectional view of an assembled bone fixation apparatus 100. The bone fixation apparatus 100 may be manufactured from titanium, such as Ti-6A1-4V, but may be made from other materials. The apparatus 100 includes a bone fastener 200 that is typically a threaded screw that is inserted into a bone to fix the apparatus 100 to the bone. The bone may be a vertebra and the bone fastener 200 can be threaded into the pedicle of the vertebra when the apparatus 100 is used to support or stabilize the spine. The bone fastener 200 includes a head that is captured within a receiver cup 300, alternatively referred to as a shell.

A saddle or sleeve 700 is also captured in the receiver cup 300 and is positioned over the bone fastener 200. The saddle includes a spherical or concave surface that engages the head of the bone fastener 200. Additionally, the saddle 700 includes a cylindrical contoured surface or some other concave surface opposite the surface that engages the bone fastener 200. The cylindrical contoured surface of the saddle 700 engages a rod 110. The rod 110, also referred to as a support rod or a stabilization rod, extends through the receiver cup 300.

A cap 800 having an internally threaded hole is positioned on top of, and is attached to, the receiver cup 300. The cap 800 can include grooves or flanges that engage complementary grooves or flanges on the receiver cup 300 as shown in areas designated 500 in FIG. 1. The grooves or flanges on each of the cap 800 and the receiver cup 300 may extend only partially around the engagement surface. Thus, the cap 800 can engage and attach to the receiver cup 300 by positioning the cap 800 on top of the receiver cup 300 and rotating the cap 800 approximately one quarter turn.

A threaded compression member 1000 is advantageously engaged in the internally threaded hole in the cap 800. As the compression member 1000 is screwed downward into the receiver cup 300, downward pressure is applied to the support rod 110 and the saddle 700. The compression member 1000 can be tightened to clamp the support rod 110 in a fixed position relative to the receiver cup 300 and bone fastener 200.

Two or more bone fixation apparatuses 100 can be fixed to the same support rod 110. A first bone fixation apparatus 100 can be attached to a first vertebra and a second bone fixation apparatus 100 can be attached to a second vertebra. The same support rod 110 can be positioned in both bone fixation apparatuses 100 thereby stabilizing the spine as is well known in the art.

Figures 2A, 2B:
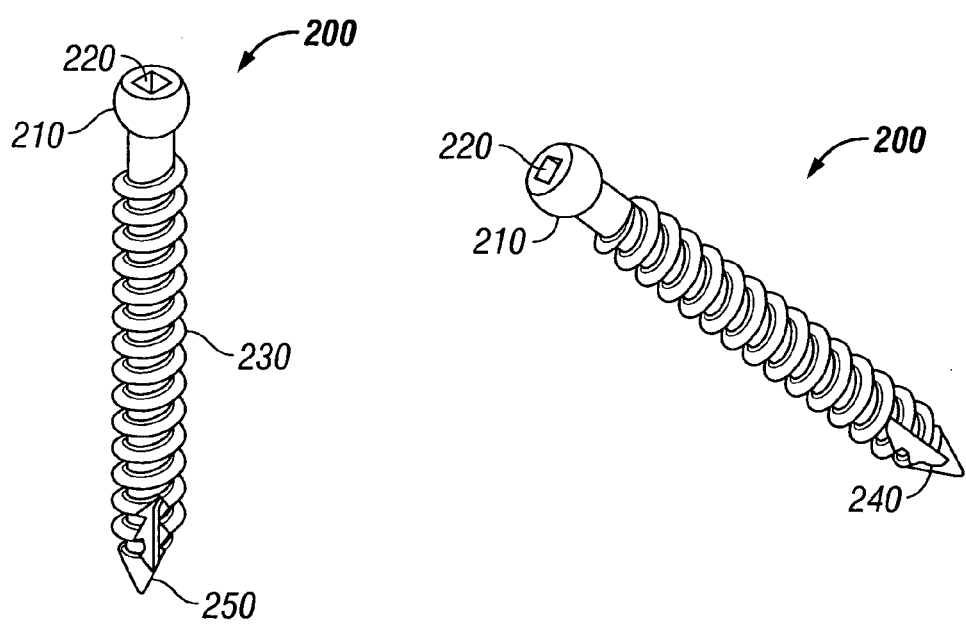
FIGS. 2A-2B are views of a bone fastener.

FIGS. 2A-2B are detailed views of one embodiment of a bone fastener 200. The bone fastener 200 is shown as a threaded screw. However, the bone fastener 200 can also be a barbed rod, a hook, a nail, a staple, an eyelet, an expanding joint, a pressed rod, a clamp, a bonding pad, and the like, or some other means for fastening to a bone.

The bone fastener 200 includes a head 210 having a drive section 220, a threaded body 230, and a tip 250 for insertion into the bone. The head 210 can be a spherical head or can have a convex lower surface for engaging an inner surface of the receiver cup 300. The head 210 need not be completely spherical, but may be spherical for substantially the surface that engages the receiver cup 300. The spherical shape of the head 210 allows a degree of movement of the receiver cup 300 about the head 210 such that the position of the receiver cup 300 may float prior to being clamped to the bone fastener 200.

The shape of the head 210 need not be spherical, but may be any surface, including curved or angular surfaces. The bottom of the head 210 that engages the receiver cup 300 may be convex or concave and typically complements the inner engagement surface of the receiver cup 300. Thus, where the bottom of the head 210 on the bone fastener 200 has a convex shape, the inner engagement surface of the receiver cup 300 typically has a concave surface.

The head 210 of the bone fastener 200 also includes a drive section 220 that may be a recess in the head 210 or an extension from the head 210 to allow the bone fastener 200 to be driven into the bone. In one embodiment, the drive section 220 is a square recess placed in the top of the head 210. The drive section 220 may alternatively be a cross recess, a slot, a hexagonal recess, a pentagonal recess, a square extension, a hexagonal extension, and the like, or some other means for receiving a driving force.

The bone fastener 200 also includes a tip 250 that is typically pointed to facilitate entry into the bone. Additionally, where the bone fastener 200 includes the threaded body 230, a groove 240 may extend from the tip 250 end upward through the first few threads. The groove 240 is configured such that the bone fastener 200 is a self tapping threaded fastener.

Figure 3A:
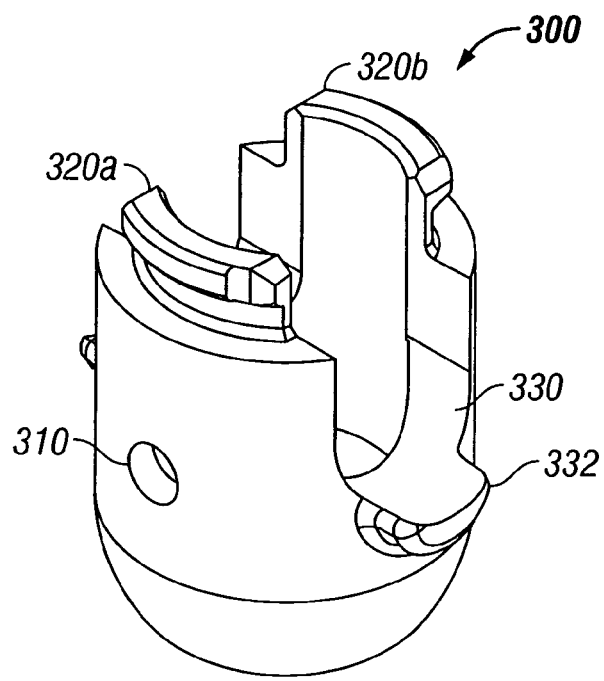
FIGS. 3A-3B are views of a receiver cup.
Figure 3B:
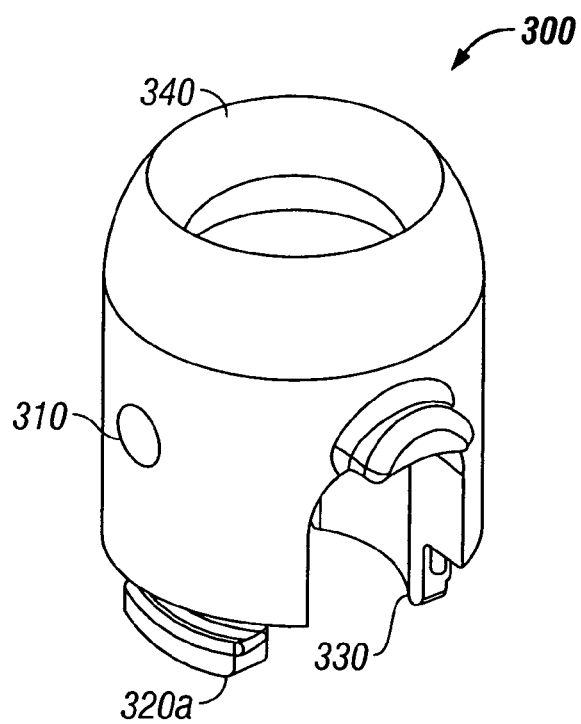

FIGS. 3A-3B are detailed views of a receiver cup 300. The receiver cup 300 includes one or more locating holes or recesses 310. A tool may be positioned in the locating hole 310 to allow the receiver cup 300 to be positioned or placed during surgery. The receiver cup 300 also includes one or more cutouts 330, grooves, or recesses to engage the support rod 110. The cutouts 330 typically extend to the upper surface of the receiver cup 300 to allow the support rod 110 to be positioned in the receiver cup 300 without requiring the rod 110 to be threaded through an opening in the receiver cup 300. The cutouts 330 typically have a contoured surface that engages the support rod 110. The cutout 330 may have a contoured surface that is substantially equal to, or slightly larger than, an outer radius of the support rod 110. Support flanges 332 may extend from substantially the location of the contoured surface of the cutout 330 to provide additional support from the support rod 110.

The receiver cup 300 is configured to capture the head 210 of the bone fastener 200. A beveled surface 340 may be provided on the bottom of the receiver cup 300 around a hole through which the bone fastener 200 extends. The beveled surface 340 provides clearance to allow the receiver cup 300 to be angled from an axis of the bone fastener 200.

A top of the receiver cup 300 is open to allow insertion of the support rod 110. Flanges 320a and 320b, also referred to as receiver flanges or receiver engagement portions, are positioned around the top of the receiver cup 300 and are used to locate and engage complementary flanges on the cap 800. The flanges 320a and 320b typically do not extend completely around the top surface of the receiver cup 300. Each of the flanges 320a and 320b may only extend one quarter, or somewhat less, of the way around the top of the receiver cup 300 such that an approximately equal area, or somewhat more, around the top of the receiver cup 300 does not have any flange. The flanges 320a and 320b thus may surround approximately one half or less of the perimeter of the receiver cup 300 forming a one quarter turn engagement with the cap.

FIG. 4 provides a top view of the receiver cup 300 and shows the placement of the flanges 320a and 320b around a portion of the top of the receiver cup 300. The flanges 320a and 320b are positioned such that at least one portion of the top of the receiver cup does not have a flange.

Each of the flanges 320a and 320b includes a stop 322a and 322b or locator that is used to locate and position the cap 800 on the receiver cup 300. The stops 322a and 322b provide a positive indication that the cap 800 is correctly positioned on the receiver cup 300. Additionally, the stops 322a and 322b ensure secure engagement of the receiver cup 300 with the cap 800. In one embodiment, the stops 322a and 322b comprise recesses in the flanges 320a and 320b.

Although the receiver cup 300 is shown with two flanges, 320a and 320b, any number of flanges 320 may be used. The flanges 320 may be uniformly spaced around the opening of the receiver cup 300 or may have irregular spacing. Additionally, although flanges having a uniform width and height are shown, the flanges may have increasing, decreasing, or irregular widths and heights, forming slidably coupled engagement portions. Additionally, the receiver cup 300 is not limited to using flanges to locate the cap 800 but can alternatively or in combination use grooves, cams, tabs, pawls, ratchets, holes, fingers, springs, detents, cogs, and the like, some other means for engaging the cap 800, or some other engagement means.

FIGS. 5A-5B provide side views of the receiver cup 300 of FIGS. 3A and 3B and show the extension of the support flange 322 from the body of the receiver cup 300. Additionally, the openings between the flanges 320a and 320b are shown to be located at substantially the same location of the cutout 330.

FIG. 6 is a view of detail area A from FIG. 4. FIG. 6 shows a placement of a stop 322a in one of the flanges 320a. The stop 322a is shown as a contoured recess in the flange 322a. However, the stop 322a can alternatively be an angular recess, a protrusion, a recess in the upper or lower surface of the flange 320a, a protrusion in the upper or lower surface of the flange 320a, a step, and the like, or some other positive retention structure.

FIGS. 7A-7B are views of the saddle 700. The saddle 700 is placed in the receiver cup 300 over the head 210 of the bone fastener 200 and beneath the support rod 110. Clamping force applied to the support rod 110 is transferred to the saddle 700 and through the saddle 700 to the bone fastener 200. The saddle 700 includes recesses 710 that are configured to interface with a tool, such as a tool used to pick and place the saddle 700 into the receiver cup 300 during surgery. Two recesses 710 are typically positioned on opposite sides of the saddle 700 to allow the saddle 700 to be manipulated using a tool.

An upper surface 720 of the saddle 700 engages the bottom portion of the support rod 110 that extends through the receiver cup 300. The upper surface is typically a concave surface that is complementary to the shape of the support rod 110. Thus, the upper surface 720 may be a cylindrically contoured surface. Alternatively, the upper surface 720 may be an angular surface, such as a V-shaped surface that centers the support rod 110 over the head 210 of the bone fastener 200. Other upper surface 720 contours may be used, including curved and polygonal. The upper surface 720 need not be continuously concave, but may have convex portions extending outward from a generally concave outline.

A lower surface 730 of the saddle 700 engages the head 210 of the bone fastener 200. The lower surface 730 is typically a concave surface that is complementary to the shape of the fastener head 210. Where the head 210 of the bone fastener 210 is spherical, the bottom surface 730 is typically a spherical recess. Alternatively, the lower surface 730 may be an angular lower surface that contacts the head 210 of the bone fastener 200 in distinct points. The lower surface 730 need not be continuously concave, but may have convex portions extending outward from a generally concave outline.

The saddle 700 may include a hole extending through the upper and lower surfaces, 720 and 730 respectively. The hole may be included to allow a tool to access the drive section 220 of the bone fastener 200. Alternatively, the saddle 700 may be manufactured without the hole and the bone fastener 200 may be installed before placement of the saddle 700 in the receiver cup 300.

Figure 8A:
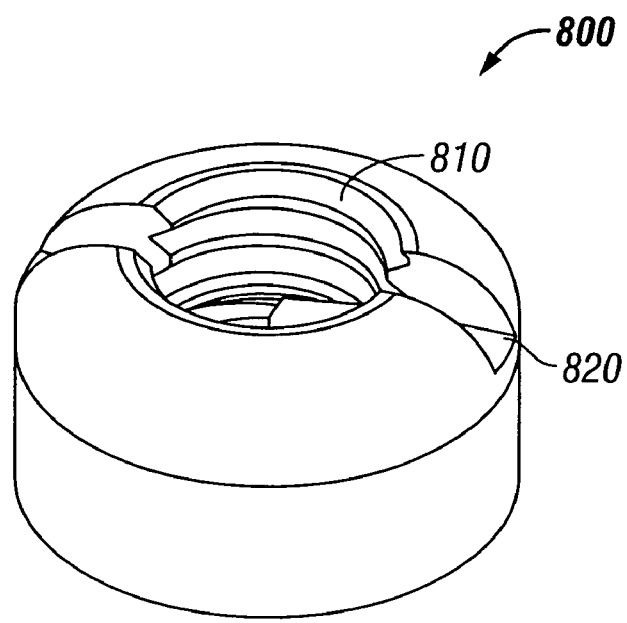
FIGS. 8A-8B are views of the cap.
Figure 8B:
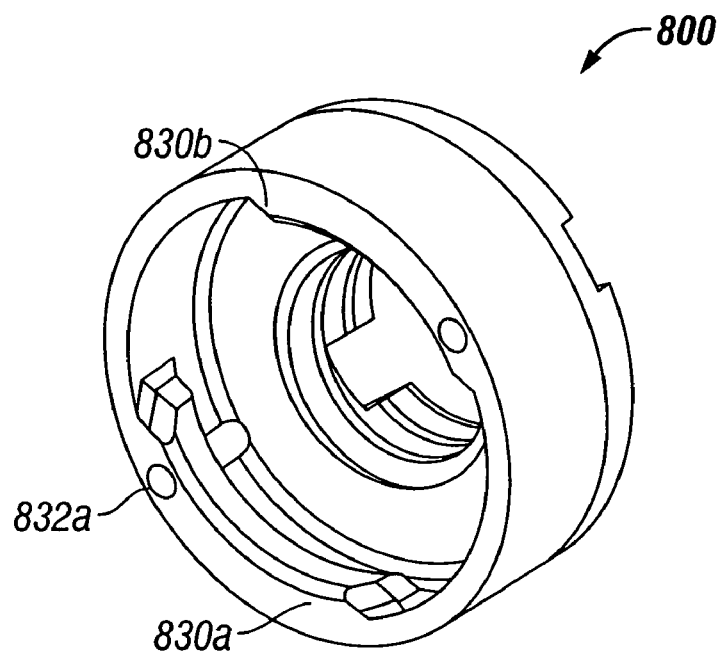

FIGS. 8A-8B are views of a cap 800 having a threaded hole 810 extending through the top of the cap 800. The top surface of the cap 800 may include notches 820 or some other structure by which a tool may interface with and rotate the cap 800. The cap 800 may use other means for engaging a tool, such as, but not limited to, one or more recesses on the top surface of the cap 800, one or more projections from the top surface of the cap 800, one or more recesses on the sides of the cap 800, one or more projections from the sides of the cap 800, and the like. Alternatively, the shape of the cap 800 may be such that engagement with a tool is facilitated. The cap 800 may be, for example, have a square outline or some other polygon outline, such as a hexagon or an octagon. As another alternative, the sides of the cap 800 may include flat surfaces in an otherwise curved surface in order to engage with a tool. Tools that interface with the cap 800 may include a wrench, a socket, a driver, or a spanner.

FIG. 8B shows a view of the underside of the cap 800 and illustrates how the cap 800 interfaces with the receiver cup 300. The opening of the cap 800 at the bottom surface includes two flanges 830a and 830b, alternatively referred to as cap engagement portions, that interface and engage the flanges 320a and 320b of the receiver cup 300. The flanges 830a and 830b on the cap 800 may alternatively be referred to as cap flanges while the flanges 320a and 320b on the receiver cup 300 may alternatively be referred to as receiver flanges.

A first flange 830a on the cap 800 can extend partially around the opening of the cap 800. The second flange 830b is positioned at the opening substantially opposite the first flange 830a. The two flanges 830a and 830b combine to extend around approximately one half the perimeter of the opening. As described earlier, the flanges 320a and 320b on the receiver cup 300 also encompass approximately one half of the perimeter of the opening of the receiver cup 300.

The cap 800 engages the receiver cup 300 by aligning the flanges 830a and 830b in the cap 800 with the openings between the flanges 320a and 320b in the receiver cup. The cap 800 is then rotated such that the cap flanges 830a and 830b are engaged in the groove defined by the receiver cup flanges 320a and 320b and the body of the receiver cup 300. Thus, once the cap 800 is aligned on the receiver cup 300, the cap 800 is installed by rotating the cap 800 one quarter turn relative to the receiver cup 300.

As was the case with the receiver cup 300, the cap is not limited to having two flanges 830a and 830b. Instead, the cap 800 may have any number of flanges and the number of flanges on the cap 800 may or may not coincide with the number of flanges 320a and 320b on the receiver cup 300. For example, the receiver cup 300 may have two flanges 320a and 320b and the cap 800 may have four flanges configured to engage the two flanges 320a and 320b on the receiver cup 300. Alternatively, the cap 800 may have 1, 2, 3, 4, 6, 8, 10, 12, or 16 flanges. The flanges 830a and 830b on the cap 800 may be uniformly spaced around the opening of the cap 800 or may have irregular spacing. Additionally, the flanges 830a and 830b typically are the same size but are not limited to having the same size. Regardless of the number of flanges, the cap engages with the receiver cup by rotating less than one full turn or rotation and typically less than one half turn. The cap can engage the receiver cup by rotating greater than zero and less than one quarter, one half, or one full turn or rotation.

The cap 800 is not limited to using flanges 830a and 830b but may use other structures that interface with complementary structures on the receiver cup 300. The cap may include cap engagement portions that slidably engage with receiver engagement portions, thereby coupling the cap to the receiver cup. Other structures include, for example, grooves, cams, tabs, pawls, ratchets, holes, fingers, springs, detents, cogs, and the like, some other means for engaging the receiver cup, or some other complementary engagement means.

The cap 800 also includes recesses 832a and 832b positioned near one end of the flanges 830a and 830b, respectively. The recesses 832a and 832b are each configured to receive a press pin, locating pin, or equivalent structure for engaging the stops, 322a and 322b, on the receiver cup flanges 320a and 320b. Alternatively, the cap 800 may be machined to include a ridge instead of having the locating pin. When the locating pins are inserted into the recesses 832a and 832b, the cap 800 can be positively located and secured to the receiver cup 300.

As the cap 800 is rotated on the receiver cup 300, the flanges 830a and 830b engage the complementary flanges 320a and 320b on the receiver cup 300. The engagement of the flanges, for example 830a with 320a, secure the cap 800 to the receiver cup 300 in a vertical direction and prevent vertical separation of the two pieces. As the cap 800 is rotated further, the locating pin in the recess, for example 832a, engages the complementary stop 322a in the receiver flange 320a. The locating pin in the cap 800 thus locates on the stop 322a substantially preventing further rotational movement of the cap 800 relative to the receiver cup 300. The cap 800 is not permanently installed, however. If sufficient rotational force is applied to the cap 800, the engagement of the locating pin with the stop 322a may be overcome and the cap 800 separated from the receiver cup 300.

Figure 9C:
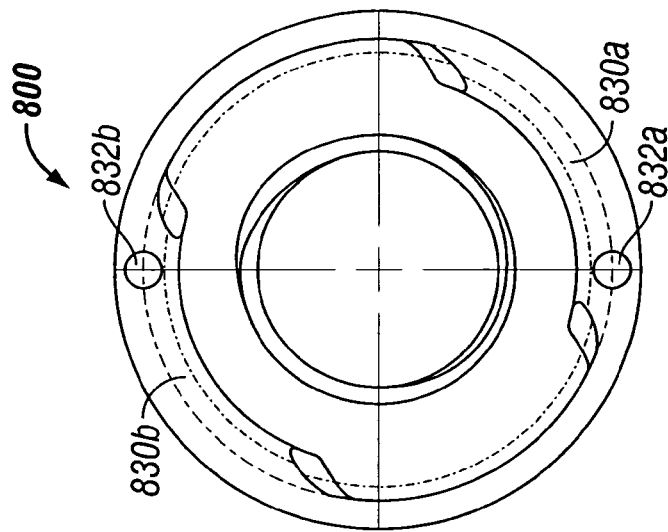
FIGS. 9A-9C are additional views of the cap.
Figure 9B:
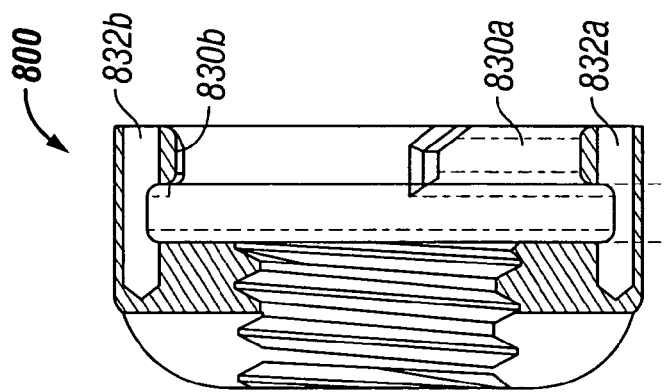
Figure 9A:
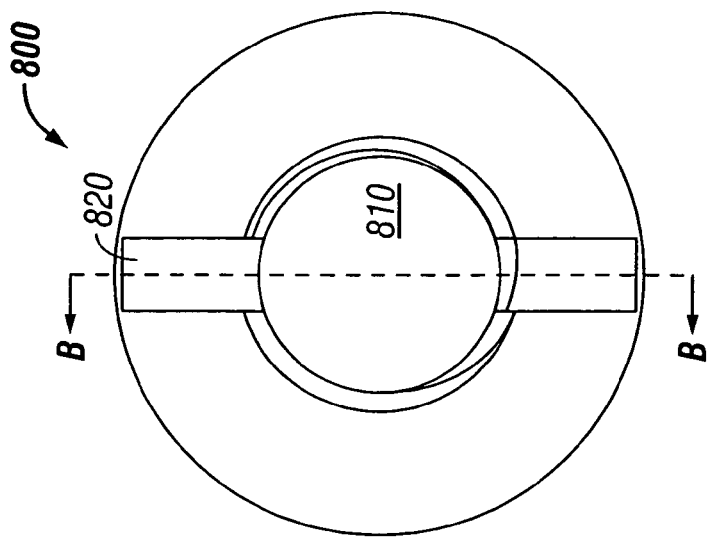

FIGS. 9A-9C show additional views of the cap 800. FIG. 9A shows the threaded hole 810 extending through the surface of the cap 800. Additionally, a notch 820 on the top surface of the cap 800 allows the cap to be rotated with a tool, such as a flat blade.

FIG. 9B is a sectional view of the cap 800. The two flanges 830a and 830b are shown positioned adjacent to the bottom surface of the cap 800. FIG. 9B also clearly illustrates the space between a flange 830a and an inner surface of the cap 800. The complementary flange 320a from the receiver cup 300 engages the cap 800 in this space. The space advantageously has dimensions that approximate the dimension of the flange 320a on the receiver cup 300.

FIG. 9C shows a bottom view of the cap 800. The position of the recesses 832a and 832b, and thus the positions of the locating pins, is shown at near one end of the flanges 830a and 830b. A first recess 832a is located near one end of the first flange 830a and a second recess 832b is located near an end of the second flange 832b. The first recess 832a is advantageously located substantially opposite the center of the cap 800 from the second recess 832b. The placement of the recesses 832a and 832b shown in FIG. 9C is advantageous for a quarter turn clockwise rotation of the cap 800 onto the receiver cup 300. Of course, the recesses 832a and 832b may be placed on the opposite ends of the flanges 830a and 830b to facilitate a counterclockwise quarter turn engagement of the cap 800 with the receiver cup 300.

Figure 10C:
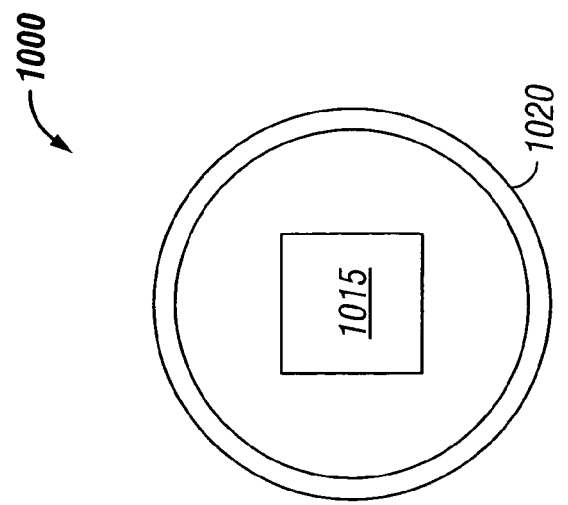
FIGS. 10A-10C are views of a compression member.
Figure 10B:
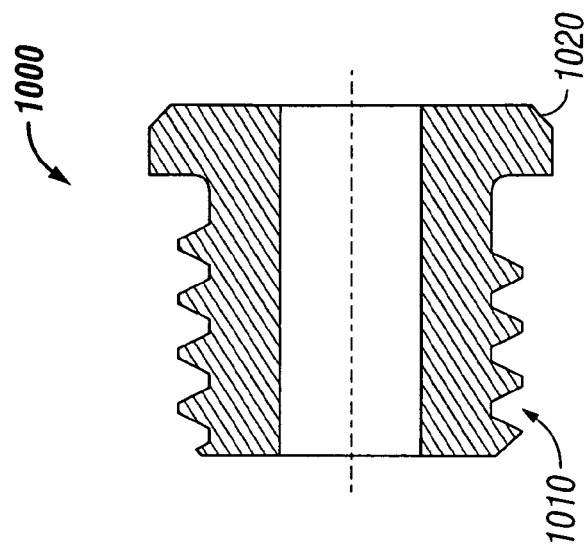
Figure 10A:
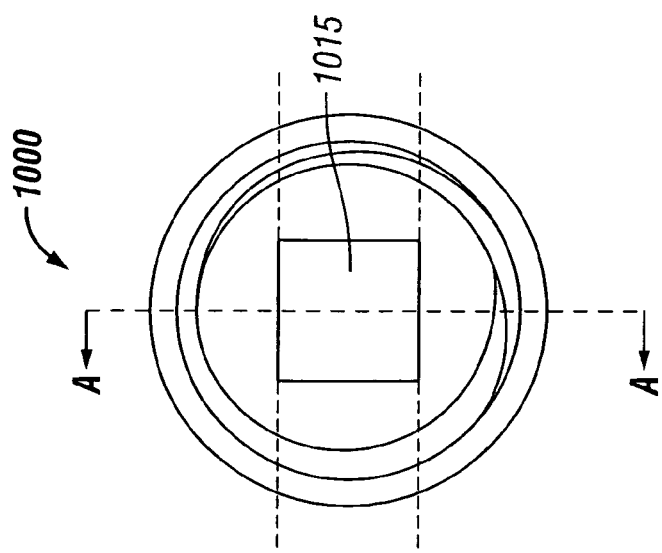

FIGS. 10A-10C are views of a compression member 1000. The compression member 1000 is advantageously a threaded fastener that engages with the threaded hole 810 of the cap 800. The compression member 1000 includes a drive receiver 1015 that may be a hole that extends through the entire length of the compression member 1000. The drive receiver 1015 is shown as a square drive hole, but may be any configuration that allows for the compression member 1000 to be screwed downward into the cap 800. For example, the drive receiver 1015 may be a hexagonal hole or recess, a square recess, a polygonal recess, a slot, a cross recess, a protrusion, a hexagonal protrusion, a square protrusion, or some other means for receiving a driving force.

The compression member includes a head portion 1020 and a body portion 1010. The head portion 1020 may be configured to receive the driving force. Additionally, the compression member 1000 may not include a head portion 1020 to allow the compression member 1000 to be screwed down into the cap 800 such that the top surface of the compression member 1000 is flush with or below the top surface of the cap 800. The body portion 1010 is threaded to engage with complementary inside threads of the threaded hole 810 in the cap 800. The compression member 1000 is shown in FIG. 9B as having a substantially flat lower surface, but the surface may also be irregular, concave, or convex.

Thus, the bone fixation apparatus shown in FIGS. 1-10 and discussed in the corresponding descriptions can be inserted without having to thread the compression member into the cap during surgery. The bone fastener can be a pedicle screw that is inserted into a vertebra. The head of the bone fastener is captured in the receiver cup. After the bone fastener is inserted in the vertebra, the saddle can be inserted into the receiver cup over the head of the bone fastener. The support or stabilization rod can then be adjusted to conform to the spine, if desired. A portion of the support rod is then placed into the receiver cup through cutouts in the receiver cup. The compression member can be pre-assembled into the cap prior to surgery. This eliminates the need to thread a compression member into the bone fixation apparatus during the course of surgery. The pre-assembled cap with compression member is then positioned onto the receiver cup. The cap is engaged and secured to the receiver cup by rotating the cap approximately one quarter turn relative to the receiver cup. The cap is positively engaged and located to the receiver cup when the locating pins on the cap align with the stops in the receiver cup. The engagement of the locating pins with the stops also provides positive feedback to the operator to indicate that the cap is securely installed onto the receiver cup. Final adjustments to the support rod and receiver cup can then be made and the compression member can then be tightened down fixing the position of the receiver cup, support rod, and bone fastener. Two or more bone fixation apparatuses can share the same support rod and can thus provide stabilization of adjacent vertebrae. The bone fixation apparatus can thus be used to support and stabilize the spine during and after surgery.

Connections, couplings, and engagements have been described with respect to various devices or elements. The connections and couplings can be direct or indirect. A connection between a first and second device can be a direct connection or can be an indirect connection. An indirect connection or engagement can include elements interposed between the first device and the second device.

The above description of the disclosed embodiments is provided to enable any person skilled in the art to make or use the invention. Various modifications to these embodiments will be readily apparent to those skilled in the art, and the generic principles defined herein can be applied to other embodiments without departing from the spirit or scope of the invention. Thus, the invention is not intended to be limited to the embodiments shown herein but is to be accorded the widest scope consistent with the principles and novel features disclosed herein.

What is claimed is:

1. A bone fixation apparatus, comprising:

a receiver cup comprising at least one receiver engagement portion, said receiver engagement portion comprising a pair of opposed cup flanges, each extending partially around a top outer surface of said receiver, the receiver cup additionally comprising a pair of mating stops, said mating stops comprising recesses in said cup flanges cup; and a cap comprising at least one cap engagement portion that slidably engages the at least one receiver engagement portion when rotated on the receiver cup less than one full rotation, said cap engagement portion comprising a pair of opposed cup flanges, each extending partially around a bottom inner surface of said cap; the cap additionally comprising a pair of mating stops, said mating stops comprising pins extending upward through openings in said cap flanges;

wherein a top surface of said cap engagement portion provides a non-threaded engagement with a bottom surface of said receiver engagement portion and additionally comprises a notch on the top surface of the cap aligned with the opposed flanges indicating flange position relative to the receiver cup when in an engaged configuration; and wherein said mating stops on said receiver engagement portion and said mating stops on said cap engagement portion are configured to engage said cap to said receiver cup upon about one quarter turn of said cap on said receiver cup.

2. The bone fixation apparatus of claim 1, further comprising:

a bone fastener having a head and a body, the head captured in the receiver cup and the body extending through the receiver cup; and a support rod having a portion extending into the receiver cup through at least one cutout in the receiver cup.

3. The bone fixation apparatus of claim 2, further comprising:

a compression member coupled to the cap and configured to fix the position of the support rod relative to the receiver cup.

4. The bone fixation apparatus of claim 2, further comprising a saddle interposed between the support rod and the head of the bone fastener.

5. The bone fixation apparatus of claim 2, wherein the bone fastener comprises a threaded fastener.

6. The bone fixation apparatus of claim 2, wherein the bone fastener comprises a pedicle screw.

7. The bone fixation apparatus of claim 1, wherein the at least one receiver engagement portion surrounds approximately one half of a perimeter of the receiver cup.

8. The bone fixation apparatus of claim 1, wherein the at least one cap engagement portion slidably engages the at least one receiver engagement portion when rotated on the receiver cup less than one half turn.

9. The bone fixation apparatus of claim 1, wherein the at least one cap engagement portion slidably engages the at least one receiver engagement portion when rotated on the receiver cup by one quarter turn.

* * * * *